United States Patent
Napolitano et al.

(10) Patent No.: US 8,840,644 B2
(45) Date of Patent: Sep. 23, 2014

(54) TOGGLE BOLT SUTURE ANCHOR

(75) Inventors: Anthony P. Napolitano, Chappaqua, NY (US); Jeffrey Wyman, Naples, FL (US)

(73) Assignee: Howmedica Osteonics Corp., Mahwah, NJ (US)

( * ) Notice: Subject to any disclaimer, the term of this patent is extended or adjusted under 35 U.S.C. 154(b) by 129 days.

(21) Appl. No.: 13/070,692

(22) Filed: Mar. 24, 2011

(65) Prior Publication Data

US 2012/0245630 A1  Sep. 27, 2012

(51) Int. Cl.
*A61B 17/04* (2006.01)

(52) U.S. Cl.
CPC ..... *A61B 17/0401* (2013.01); *A61B 2017/0404* (2013.01); *A61B 2017/0414* (2013.01); *A61B 2017/0417* (2013.01); *A61B 2017/0496* (2013.01); *A61B 17/0483* (2013.01); *A61B 2017/0409* (2013.01); *A61B 2017/0411* (2013.01)
USPC .......................................... 606/232; 606/139

(58) Field of Classification Search
USPC ................... 606/232, 139, 144, 151
See application file for complete search history.

(56) References Cited

U.S. PATENT DOCUMENTS

| | | | |
|---|---|---|---|
| 860,636 A | 7/1907 | Church | |
| 2,485,531 A | 10/1949 | Dzus et al. | |
| 3,332,118 A | 7/1967 | Temple et al. | |
| 3,976,079 A | 8/1976 | Samuels et al. | |
| 4,075,924 A | 2/1978 | McSherry et al. | |
| 4,265,231 A | 5/1981 | Scheller, Jr. et al. | |
| 4,294,156 A | 10/1981 | McSherry et al. | |
| 4,439,079 A | 3/1984 | Losada | |
| 4,590,928 A | 5/1986 | Hunt et al. | |
| 4,650,386 A | 3/1987 | McSherry et al. | |
| 4,782,451 A | 11/1988 | Mazzarella et al. | |
| 5,002,546 A | 3/1991 | Romano | |
| 5,030,219 A | 7/1991 | Matsen, III et al. | |
| 5,139,520 A | 8/1992 | Rosenberg | |
| 5,242,457 A | 9/1993 | Akopov et al. | |
| 5,269,809 A | 12/1993 | Hayhurst et al. | |
| 5,306,301 A | 4/1994 | Graf et al. | |
| 5,374,269 A | 12/1994 | Rosenberg | |
| 5,395,188 A | 3/1995 | Bailey et al. | |
| 5,409,490 A | 4/1995 | Ethridge | |
| 5,437,677 A | 8/1995 | Shearer et al. | |
| 5,454,821 A | 10/1995 | Harm et al. | |
| 5,464,425 A | 11/1995 | Skiba | |

(Continued)

FOREIGN PATENT DOCUMENTS

WO  2006/130693 A2  12/2006

OTHER PUBLICATIONS

European Search Report, EP 12150748, May 8, 2012.

(Continued)

*Primary Examiner* — Gregory Anderson
(74) *Attorney, Agent, or Firm* — Lerner, David, Littenberg, Krumholz & Mentlik, LLP

(57) ABSTRACT

In one embodiment, the present invention may include a system for securing soft tissue relative to a bone including a tissue anchor having a substantially planar body having a channel and at least one bore hole; an inserter rod having a longitudinal length and adapted to be positioned within the channel of the tissue anchor; and an engagement structure on at least one of the channel or the inserter rod adapted to removeably affix the tissue anchor to the inserter rod.

17 Claims, 4 Drawing Sheets

(56) References Cited

U.S. PATENT DOCUMENTS

| | | | |
|---|---|---|---|
| 5,484,451 A | 1/1996 | Akopov et al. |
| 5,496,348 A | 3/1996 | Bonutti |
| 5,522,846 A | 6/1996 | Bonutti |
| 5,573,543 A | 11/1996 | Akopov et al. |
| 5,628,740 A | 5/1997 | Mullane |
| 5,645,588 A | 7/1997 | Graf et al. |
| 5,769,894 A | 6/1998 | Ferragamo |
| 5,868,789 A | 2/1999 | Huebner |
| 5,921,986 A | 7/1999 | Bonutti |
| 6,010,525 A | 1/2000 | Bonutti et al. |
| 6,045,574 A | 4/2000 | Thal |
| 6,056,752 A | 5/2000 | Roger |
| 6,068,648 A | 5/2000 | Cole et al. |
| 6,099,568 A | 8/2000 | Simonian et al. |
| 6,110,207 A | 8/2000 | Eichhorn et al. |
| 6,117,139 A | 9/2000 | Shino |
| 6,161,999 A | 12/2000 | Kaye et al. |
| 6,171,310 B1 | 1/2001 | Giordano et al. |
| 6,187,011 B1 | 2/2001 | Torrie |
| 6,267,767 B1 | 7/2001 | Strobel et al. |
| 6,287,065 B1 | 9/2001 | Berlin |
| 6,419,678 B1 | 7/2002 | Asfora |
| 6,440,134 B1 | 8/2002 | Zaccherotti et al. |
| 6,451,030 B2 | 9/2002 | Li et al. |
| 6,482,210 B1 | 11/2002 | Skiba et al. |
| 6,517,578 B2 | 2/2003 | Hein |
| 6,533,802 B2 | 3/2003 | Bojarski et al. |
| 6,562,071 B2 | 5/2003 | Jarvinen |
| 6,569,187 B1 | 5/2003 | Bonutti et al. |
| 6,638,279 B2 | 10/2003 | Bonutti |
| 6,736,829 B1 | 5/2004 | Li et al. |
| 6,773,436 B2 * | 8/2004 | Donnelly et al. ............ 606/232 |
| 6,923,824 B2 | 8/2005 | Morgan et al. |
| 7,037,324 B2 | 5/2006 | Martinek |
| 7,041,120 B2 | 5/2006 | Li et al. |
| 7,087,073 B2 | 8/2006 | Bonutti |
| 7,090,690 B2 | 8/2006 | Foerster et al. |
| 7,097,654 B1 | 8/2006 | Freedland |
| 7,108,710 B2 | 9/2006 | Anderson |
| 7,163,540 B2 | 1/2007 | Martello |
| 7,736,108 B1 | 6/2010 | Bruce et al. |
| 7,803,173 B2 | 9/2010 | Burkhart et al. |
| 7,819,898 B2 | 10/2010 | Stone et al. |
| 7,875,057 B2 | 1/2011 | Cook et al. |
| 7,896,907 B2 * | 3/2011 | McDevitt et al. ............ 606/304 |
| 7,934,506 B2 * | 5/2011 | Woodson et al. ............ 128/860 |
| 8,109,965 B2 | 2/2012 | Stone et al. |
| 8,128,669 B2 | 3/2012 | Bonutti |
| 8,147,514 B2 | 4/2012 | Bonutti |
| 8,231,674 B2 | 7/2012 | Albertorio et al. |
| 8,439,946 B2 | 5/2013 | Miller et al. |
| 8,506,596 B2 | 8/2013 | Stone et al. |
| 2001/0025181 A1 | 9/2001 | Freedlan |
| 2001/0041938 A1 | 11/2001 | Hein |
| 2002/0019634 A1 | 2/2002 | Bonutti |
| 2002/0183762 A1 | 12/2002 | Anderson et al. |
| 2004/0015171 A1 | 1/2004 | Bojarski et al. |
| 2004/0046009 A1 | 3/2004 | Weisenberg et al. |
| 2004/0127907 A1 | 7/2004 | Dakin et al. |
| 2004/0236419 A1 | 11/2004 | Milo |
| 2004/0243128 A1 | 12/2004 | Howland |
| 2004/0260298 A1 | 12/2004 | Kaiser et al. |
| 2005/0038427 A1 | 2/2005 | Perriello et al. |
| 2005/0090827 A1 | 4/2005 | Gedebou |
| 2005/0234460 A1 | 10/2005 | Miller |
| 2005/0240189 A1 | 10/2005 | Rousseau et al. |
| 2005/0267479 A1 | 12/2005 | Morgan et al. |
| 2005/0273138 A1 | 12/2005 | To et al. |
| 2006/0052786 A1 | 3/2006 | Dant et al. |
| 2006/0241656 A1 | 10/2006 | Starksen et al. |
| 2006/0265011 A1 | 11/2006 | Bonutti |
| 2007/0016208 A1 | 1/2007 | Thornes |
| 2007/0049944 A1 | 3/2007 | Stone et al. |
| 2007/0100353 A1 | 5/2007 | Chudik |
| 2007/0112338 A1 | 5/2007 | Cohen et al. |
| 2007/0118132 A1 | 5/2007 | Culbert et al. |
| 2007/0142835 A1 | 6/2007 | Green et al. |
| 2007/0225719 A1 | 9/2007 | Stone et al. |
| 2007/0233241 A1 | 10/2007 | Graf et al. |
| 2007/0270857 A1 | 11/2007 | Lombardo et al. |
| 2008/0046009 A1 | 2/2008 | Albertorio et al. |
| 2008/0086138 A1 | 4/2008 | Stone et al. |
| 2008/0109038 A1 | 5/2008 | Steiner et al. |
| 2008/0188935 A1 | 8/2008 | Saylor et al. |
| 2008/0287991 A1 | 11/2008 | Fromm |
| 2009/0018654 A1 | 1/2009 | Schmieding et al. |
| 2009/0105754 A1 | 4/2009 | Sethi |
| 2009/0204146 A1 | 8/2009 | Kaiser et al. |
| 2009/0234387 A1 | 9/2009 | Miller et al. |
| 2010/0004683 A1 | 1/2010 | Hoof et al. |
| 2010/0268273 A1 | 10/2010 | Albertorio et al. |
| 2011/0054526 A1 | 3/2011 | Stone et al. |
| 2011/0224764 A1 | 9/2011 | Kulle |
| 2011/0301708 A1 | 12/2011 | Stone et al. |
| 2012/0116452 A1 | 5/2012 | Stone et al. |
| 2013/0023929 A1 | 1/2013 | Sullivan et al. |
| 2013/0090687 A1 | 4/2013 | Lebeau et al. |
| 2013/0103085 A1 | 4/2013 | Hart et al. |
| 2013/0123843 A1 | 5/2013 | Chan et al. |
| 2013/0131723 A1 | 5/2013 | Snell et al. |
| 2013/0238025 A1 | 9/2013 | Howard et al. |
| 2013/0253581 A1 | 9/2013 | Robison |

OTHER PUBLICATIONS

Case No. 2:07-CV-335-TJW, Doc. 82, *Smith & Nephew, Inc.* v. *Arthrex, Inc.*, Infringment of USPN 5,306,301 and 5,645,588, 47 pages, Nov. 20, 2009.

Orthopedics Today, Point/Counterpoint ACL Reconstruction, Mar. 7, 2008.

Smith & Nephew, Endobutton CL, Fixation System, Knee Series, Technique Guide, 1999.

* cited by examiner

TOGGLE BOLT SUTURE ANCHOR

BACKGROUND OF THE INVENTION

Injuries to soft tissue and surrounding bones and joints are quite common. In particular, damage to the anterior cruciate ligament (ACL), the acromioclavicular (AC) joint, and other similar soft-tissue-to-bone connection sites are very common. Such damage may occur during participation in contact sports, a traumatic event, such as a car accident, or through general wear and tear within a joint. Typically, the soft tissue injury occurs at the soft-tissue-to-bone connection site at or near the surface of the bone.

To continue the example of a damaged ACL, when an ACL undergoes an event sufficient to cause such a tear, replacement or reconstructive ACL surgery is normally required, which will replace the damaged ACL with a new soft tissue graft. The graft is secured to the tibia and femur through a variety of known methods and devices. In many such surgeries, bone tunnels are drilled through the tibia and femur, and the tissue graft is secured within the tunnels.

One such implant which is presently used to secure a tissue graft within a bone tunnel is a tissue implant commonly referred to as a button anchor. As is well known in the art, the button anchor, in the case of a ligament replacement surgery, attaches to the tissue graft directly or with a suture or other material and suspends a portion of the graft within the bone tunnel. The remainder of the graft spans the joint and attaches to a second bone in any known fashion. The button anchor itself is positioned at the exit of the bone tunnel and rests against the surface of the bone, forming a secure platform from which the graft is held. However, one difficulty with current button anchors is the ability to properly place the button anchor against the surface of the bone in an efficient manner.

BRIEF SUMMARY OF THE INVENTION

The present invention may include various embodiments of tissue anchors and methods of using the tissue anchors to simply and efficiently secure a tissue graft within a bone tunnel. In one example, such tissue anchors and methods may be used to secure an ACL tissue graft during ACL replacement surgery, though securement of other soft tissue grafts in other locations in a patient are also envisioned.

In one embodiment, the present invention may include a system for securing soft tissue relative to a bone, comprising a tissue anchor including a substantially planar body having a channel and at least one bore hole; an inserter rod having a longitudinal length and adapted to be positioned within the channel of the tissue anchor; and an engagement structure on at least one of the channel or the inserter rod adapted to removeably affix the tissue anchor to the inserter rod. The engagement structure may be, for example, a taper, press-fit, shoulder, matching threads, or the like.

In another embodiment, the present invention is a system for securing soft tissue relative to a bone, comprising a tissue anchor including a substantially planar body having at least one bore hole and a first engagement structure, the first engagement structure comprising one of a hook or an eyelet; and an elongated inserter rod including a second engagement structure, the second engagement structure comprising the other of the hook or the eyelet to removeably affix the inserter rod to the tissue anchor by engagement of the first and second engagement structures.

In yet another embodiment, the present invention may include a system for securing soft tissue relative to a bone, comprising a tissue anchor including a substantially planar body having at least one bore hole and a channel; an inserter rod having a longitudinal length and adapted to be positioned within the channel of the tissue anchor; and an engagement structure adapted to be positioned within the channel to removeably affix the tissue anchor to the inserter rod. The channel may further include a first diameter at one end, a second diameter at a middle portion, and a third diameter at a second end, wherein the second diameter is smaller than the first or third diameters. Further, the engagement structure comprises a substantially cylindrical shape having a throughbore and adapted to rotate while positioned within the channel. The system may further include a guide pin which can be removeably affixed to the inserter rod.

DETAILED DESCRIPTION

The example of an ACL repair, such as an ACL replacement surgery, will be used throughout this application, though the disclosed anchors and methods may be used to repair various soft tissue injuries to re-attach the soft tissue, or a replacement graft, to a bone. For example, the disclosed anchors and methods may be used to repair an AC joint, ankle joint, elbow joint, biceps tendon, vertebral joints, or the like.

Figure 1:
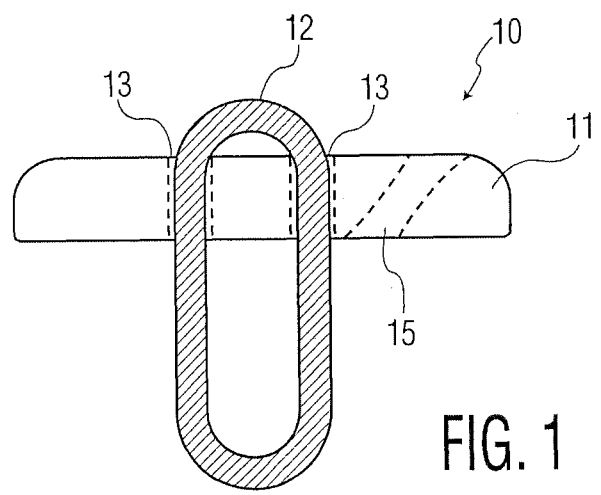
FIG. 1 illustrates one embodiment of a tissue anchor of the present invention.
Figure 2:
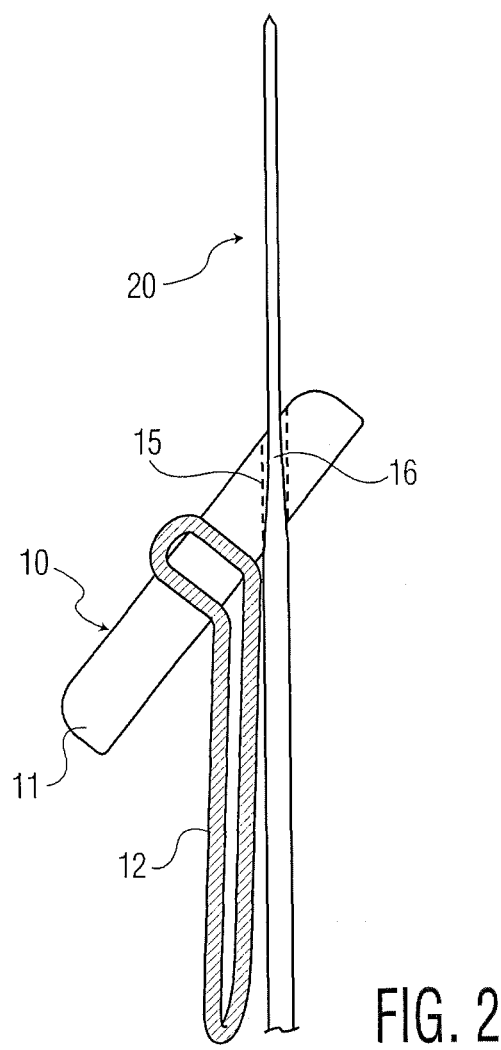
FIG. 2 illustrates the tissue anchor of FIG. 1 and an inserter rod of the present invention.

In a first embodiment, illustrated in FIGS. 1 and 2, the present invention includes a system for securing soft tissue relative to a bone, which includes a tissue anchor 10 having a body 11 which may be substantially planar, a channel 15, and at least one bore hole 13; an elongated inserter rod 20 having a longitudinal length and adapted to be positioned within the channel 15 of the tissue anchor 10; and an engagement structure (to be discussed hereinafter) on at least one of the channel or the inserter rod adapted to removeably affix the tissue anchor to the inserter rod.

A suture loop 12 may be secured within the at least one bore hole 13, which can serve as an attachment site for a tissue graft, existing soft tissue, or the like. As illustrated in FIGS. 1-4, the planar body 11 may include two bore holes, which can accommodate suture loop 12. However, other embodiments may include a planar body 11 having only a single bore hole whereby the suture loop can be secured therein using a knot, or the like. Of course, other embodiments may include more than two bore holes to accommodate, for example, additional suture loops which may be used for double bundle tissue grafts, or the like.

Continuing with this embodiment, the channel 15 passes through the tissue anchor in a direction transverse to a longitudinal axis of the body 11 of the tissue anchor. As will be explained below, the angle of the channel 15 allows for easier passage of the tissue anchor and inserter rod through a bone hole or other like pathway, by, for example, positioning the longitudinal axis of the planar tissue anchor at an acute angle to the longitudinal length of the inserter rod to form a smaller profile for passage of the inserter rod and tissue anchor through the bone hole.

Additionally, the inserter rod 20 in one embodiment may be flexible, such that the inserter rod can be forced to bend along a portion of its length, and then return to its generally original linear shape once the force has been removed. For example, upon insertion of the inserter rod and tissue anchor into a bone hole, the portion of the inserter rod adjacent to or through the channel of the tissue anchor may be bent to allow the longitudinal axis of the tissue anchor to be positioned at an even smaller angle to the general longitudinal length of the inserter rod, such that the profile of the anchor and rod are even smaller. Further, the inserter rod may bend sufficiently to position the longitudinal axis of the tissue anchor generally parallel to the general longitudinal length of the inserter rod.

The engagement structure if present forms a removeably affixed connection between the tissue anchor and the inserter rod such that the tissue anchor and inserter rod are secured to one another, but also may be taken apart from one another. For example, the engagement structure may include a taper 16 along at least a portion of the longitudinal length of the inserter rod. The taper 16 increases the diameter of the inserter rod 20 such that the enlarged diameter of the inserter rod is larger than a diameter of the channel 15. Thus, when the inserter rod 20 is positioned within the channel, the rod is passed through the channel until the taper, and larger diameter, contacts a portion of the channel, and the rod and tissue anchor 10 are affixed relative one another along this taper.

In an alternative arrangement (not shown), the inserter rod 20 includes one of more threads along at least a portion of its longitudinal length. The threaded portion is operable for interacting with a matching threaded portion positioned within at least a portion of the channel 15. Thus, as the rod is positioned within the channel, the two threaded portions contact one another and thus be rotated relative to one another to affix the rod and tissue anchor to one another. To remove the tissue anchor from the inserter rod, the threaded portions are unscrewed by rotating at least one of the two structures relative to one another. Of course, other such attachment features may also be used to affix or hold the inserter rod relative to the tissue anchor.

Figure 3:
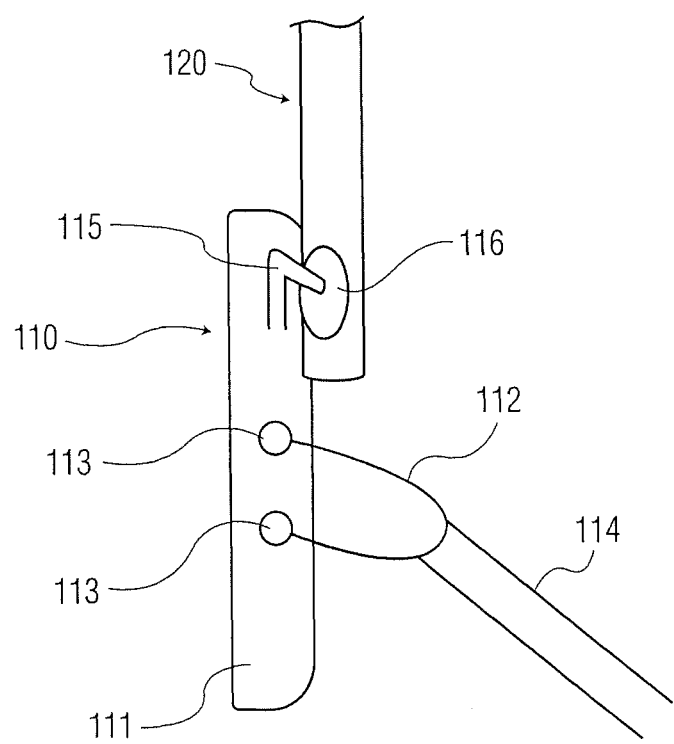
FIG. 3 illustrates another embodiment of the tissue anchor and inserter rod of the present invention.

In another embodiment of the present invention, as illustrated in FIG. 3, a system for securing soft tissue relative to a bone includes a tissue anchor 110 including a body 111 which may be substantially planar, at least one bore hole 113, and optionally an engagement structure 115 such as a hook or an eyelet to removeably affix the tissue anchor to an elongated inserter rod 120. The inserter rod 120 along its longitudinal length optionally may include an engagement structure 116 such as the other of the hook or the eyelet to removeably affix the inserter rod to the tissue anchor. As illustrated in FIG. 3, the tissue anchor engagement structure 115 in one embodiment comprises an eyelet and the engagement structure 116 of the rod 120 comprises the hook. The hook and eyelet are adapted to engage one another to secure the tissue anchor to the inserter rod.

The engagement structure 115 of the tissue anchor may be positioned towards an end portion of the substantially planar body 111, and the engagement structure 116 of the inserter rod 120 may also be positioned towards an end portion along its longitudinal length. Specifically, as illustrated in FIG. 3, the engagement structure 116 of the inserter rod 120 is positioned at a trailing end of the inserter rod. As will be discussed below, as the inserter rod 120 is pulled through a bone tunnel, or like pathway, the inserter rod will carry the tissue anchor 110 on its trailing end such that the rod pulls the tissue anchor through the bone tunnel. Again, the tissue anchor 110 may be positioned, when the eyelet and hook are secured, generally parallel to the inserter rod 120 for ease of passage through the bone hole. As in FIGS. 1 and 2, the inserter rod 120 of FIG. 3 may also be flexible to better accommodate surrounding anatomy, a narrow bone tunnel, or the like, as the inserter rod and tissue anchor are passed into the patient.

A further embodiment of the present invention as illustrated in FIGS. 4A-4E includes a system for securing soft tissue relative to a bone, which includes a tissue anchor 210 comprising a body 211 which may be substantially planar, at least one bore hole 213, and a channel 215; an elongated inserter rod 220 having a longitudinal length and adapted to be positioned within the channel 215 of the tissue anchor 210; and an engagement structure 240 adapted to be positioned within the channel 215 to removeably affix the tissue anchor 210 to the inserter rod 220.

The channel 215 may pass through the tissue anchor 210 in a direction transverse to a longitudinal axis of the body 211 of the tissue anchor. As will be explained below, the angle of the channel 215 allows for easier passage of the tissue anchor 210 and inserter rod 220 through a bone hole or other like pathway. Additionally, the channel 215 may include a first diameter 217 at one end, a second diameter 218 at a middle portion, and a third diameter 219 at a second end, wherein the second diameter is smaller than the first or third diameters. As will be explained in greater detail below, the hourglass-like shape of channel 215 will provide for a specified amount of rotation of the tissue anchor 210 relative to the inserter rod 220, and will additionally provide a location for placement of an engagement structure 240.

The engagement structure 240 may be positioned within the channel 215, such as adjacent to, or at, the middle portion having the second diameter 218. In this embodiment, as specifically illustrated in FIG. 4E, the engagement structure 240 includes a substantially cylindrical shaped body 242 having a throughbore 244 and which may be adapted to rotate, relative to tissue anchor 210, while positioned within the channel 215.

The inserter rod 220 is adapted to pass through the throughbore 244 of the engagement structure 240 (see FIG. 4B) such that the inserter rod extends outwardly from both ends of the channel 215. The inserter rod 220 optionally includes a threaded portion 225 along at least a portion of its longitudinal length, and the engagement structure 240 would also include a matching thread positioned along at least a portion of the throughbore 244 to releaseably affix the engagement structure to the inserter rod upon insertion of the inserter rod into the throughbore. Alternatively, the throughbore 244 may be smooth, and the inserter rod 220 may have another element, besides the threaded portion 225, along its length to removeably affix the rod to the tissue anchor 210, via the throughbore 244, such as a taper, a shoulder, or the like.

Figure 4A:
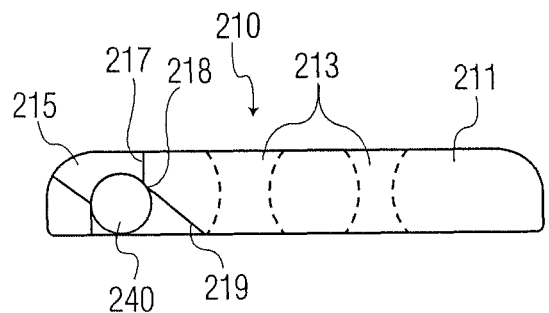
FIGS. 4A-4E illustrate a further embodiment of the tissue anchor and inserter rod of the present invention, while FIG. 4E specifically illustrates the engagement structure of FIGS. 4A-4D.
Figure 4B:
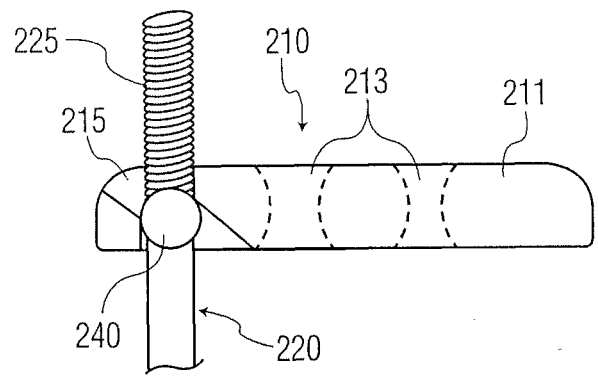
Figure 4C:
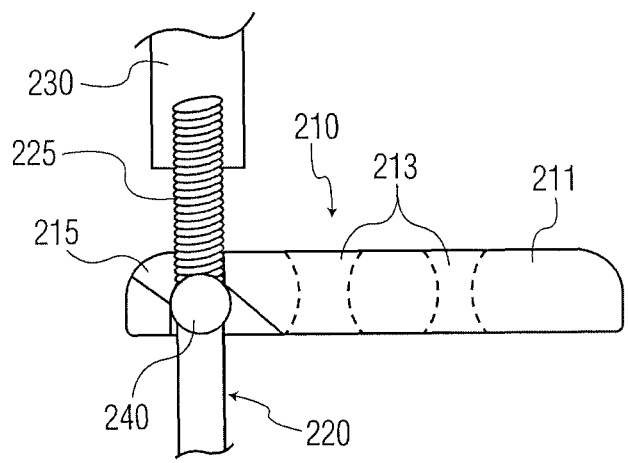
Figure 4D:
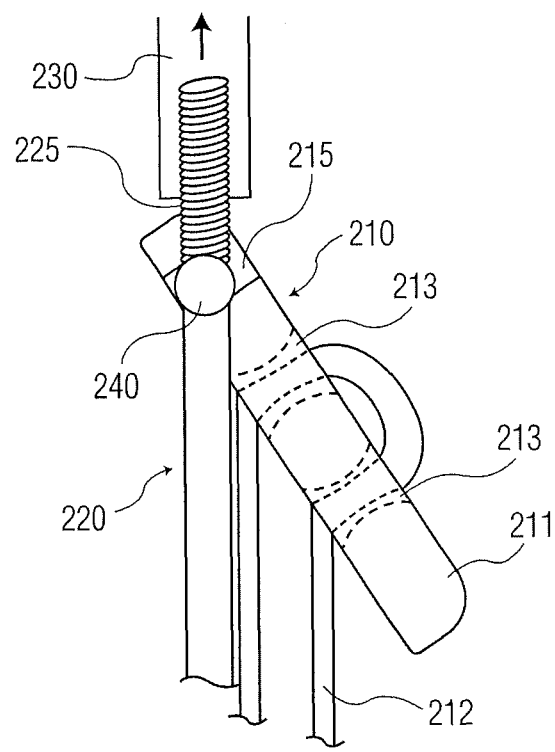
Figure 4E:
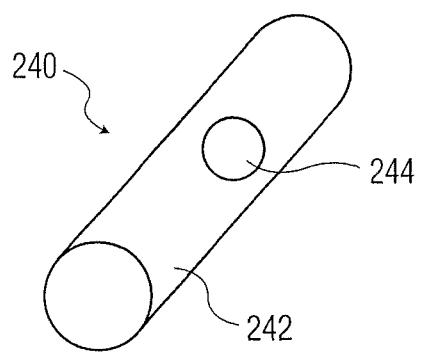

In an alternative embodiment, the engagement structure 240 may be fixedly secured to the inserter rod 220, or alternatively, these two elements may be manufactured as a single monolithic piece. In this embodiment, the threaded portion 225 may begin adjacent the engagement structure 240 and continue along only a portion of the remaining length of the inserter rod towards its leading end, or may continue to the end of the inserter rod 220, as illustrated in FIGS. 4B-4D. In this embodiment, the inserter rod, with engagement structure 240 secured thereto, is passed through channel 215 until the engagement structure contacts the inner surface of the channel, which may be adjacent to the second diameter 218. Thus, the engagement structure 240 may be removeably affixed to the tissue anchor 210 by a press-fit against the second diameter 218, or by the tissue anchor resting on the engagement structure and using gravity to remain in place. The tissue anchor 210, in this embodiment, can rotate relative to the longitudinal length of the cylindrical engagement structure 240 and inserter rod 220 (as in FIGS. 4C and 4D).

The interaction between the tissue anchor 210, engagement structure 240, and inserter rod 220 allows the tissue anchor to rotate relative to the inserter rod, as in FIGS. 4C and 4D. This rotation may be within any desired angular range, but, as illustrated, such rotation is limited by the inserter rod 220 contacting an inner surface of the channel 215, specifically the inner surface defined by the first 217 and third 219 diameters. The relative rotation occurs between the cylindrical shape of the engagement structure 240 and the channel 215 of the tissue anchor 210. Additionally, as above, the inserter rod 220 may be flexible along at least a portion of its length such that the inserter rod and tissue anchor 210 combination may have a smaller profile. For example, this allows the tissue anchor's longitudinal axis to approach or attain a generally parallel position relative to the general longitudinal length of the inserter rod, when the rod bends along its length at or near the tissue anchor.

The system may further include a guide pin 230 which may be removably affixed to the inserter rod 220 such as, for example, by threaded portion 225 and a matching threaded portion on a female engagement area in an end of the guide pin 230. Once in place, the tissue anchor 210 may be removeably affixed on the length of the inserter rod 220 between the engagement structure 240 and the guide pin 230, as illustrated in FIGS. 4C and 4D.

The various embodiments of the present invention may be used for various surgical applications such as, for example, ACL replacement surgery. Alternative variations of such tissue anchors are disclosed in U.S. Provisional App. Nos. 60/979,655 filed Oct. 12, 2007 and 61/432,481 filed Jan. 13, 2011; PCT App. No. PCT/US08/079,277 filed Oct. 9, 2008; and co-pending U.S. application Ser. No. 12/682,324 filed Apr. 9, 2010, each of which is incorporated by reference herein as if fully set forth herein.

The present invention may also be used in a method of repairing soft tissue by, for example, providing an attachment site for a soft tissue graft to a bone. Examples of such methods using alternative variations of tissue anchors are disclosed in the above-referenced patent applications incorporated by reference herein.

In one embodiment of a method of use of the tissue anchor 10 of the present invention, the method includes securing a tissue graft to suture loop 12; passing inserter rod 20 through channel 15 to removeably affix the inserter rod to the tissue anchor; pushing the inserter rod, with tissue anchor affixed, up through a bone tunnel through a bone; once the tissue anchor exits from the bone tunnel to a surface of the bone, removing the inserter rod from the tissue anchor; and pulling on one of the graft or the suture loop to seat the tissue anchor against the surface of the bone. Alternatively, the rod 20 may be positioned within the channel 15 during manufacture, in which case the method of use would instead include securing a tissue graft to suture loop 12; pushing an inserter rod 20, with a tissue anchor 10 affixed, up through a bone tunnel through a bone; once the tissue anchor exits from the bone tunnel to a surface of the bone, removing the inserter rod from the tissue anchor; and pulling on one of the graft or the suture loop to seat the tissue anchor against the surface of the bone.

The inserter rod 20 has two ends, one of which may extend to a tapered tip, such as a trocar tip or the like, to assist in passing the inserter rod through the bone tunnel and out to the surface of the bone. The inserter rod may also include a taper, a thread, or other engagement structure 16 such that upon passing the inserter rod through the channel 15, the taper of the inserter rod, for example, becomes wedged within the channel to removeably affix the anchor and rod together. Once the tissue anchor exits from the bone tunnel to the surface of the bone, the taper, thread, or the like may then be disengaged and the inserter rod may then be withdrawn from the channel. Alternatively, the channel 15 and inserter rod 20 may have matching threads such that the rod may be rotated such that the matching threads engage one another to removeably affix the anchor and rod together.

Furthermore, the inserter rod 20 used in this method may be flexible along at least a portion of its length, such that the longitudinal length of the tissue anchor 10 may be positioned at a smaller angle to the general longitudinal length of the inserter rod, when the inserter rod is bent at a position adjacent to or at the tissue anchor. For example, using FIG. 2, as the tissue anchor 10, removeably affixed to the inserter rod 20, passes through the entry of a bone tunnel, the inner surface of the tunnel may force the tissue anchor towards the general length of the inserter rod. This force may be sufficient to bend the inserter rod such that the tissue anchor can create a smaller profile in that the longitudinal axis of the tissue anchor approaches or attains a generally parallel arrangement to the general length of the inserter rod. Thus, the inserter rod forms a general S-curve along the portion of its length adjacent to the tissue anchor.

The tissue anchor 10 and inserter rod 20 may then travel through the tunnel until, as in ACL surgery, the tissue anchor exits the bone tunnel on a surface of the femur. Once the tissue anchor 10 exits the tunnel, thus relieving the force applied to it by the inner surface of the bone tunnel, the inserter rod 20 returns to its generally longitudinal shape, thereby rotating the tissue anchor back to the previous position, illustrated in FIG. 2. Returning to this position allows for better seating as the tissue anchor is now at a larger angle from the general longitudinal length of the inserter rod. Moreover, using a flexible inserter rod in this method allows the surgeon to prepare a smaller diameter bone tunnel, because of the ability of the tissue anchor 10 and inserter rod 20 to attain a reduced profile while within the bone tunnel, which may increase the likelihood of a successful surgery and recovery.

In another embodiment of a method of the present invention using tissue anchor 110, the method includes securing a tissue graft 114 to a suture loop 112; removeably affixing inserter rod 120 to tissue anchor 110 wherein one end of the inserter rod is secured to one end of the tissue anchor; pushing the inserter rod through a bone tunnel through a bone; once the other end of the inserter rod exits from the bone tunnel and past a surface of the bone, pulling on that other end of the inserter rod to pull the rod and tissue anchor completely through the bone tunnel; releasing the inserter rod from the tissue anchor; and pulling on at least one of the tissue graft or suture loop to seat the tissue anchor against the surface of the bone. The tissue anchor 110 and inserter rod 120 may be removeably affixed to one another by a first engagement structure 115 on the tissue anchor including one of a hook or an eyelet, and the elongated inserter rod 120 including a second engagement structure 116 comprising the other of the hook or the eyelet to removeably affix the inserter rod to the tissue anchor by engagement of the first and second engagement structures.

As above, one alternative may include a tissue anchor 110 and inserter rod 120 which are already removeably affixed to one another, in which case the method of use includes securing a tissue graft 114 to a suture loop 112; pushing the inserter rod through a bone tunnel through a bone; once the end of the inserter rod exits from the bone tunnel and past a surface of the bone, pulling on that end of the inserter rod to pull the inserter rod and tissue anchor completely through the bone tunnel; releasing the inserter rod from the tissue anchor; and pulling on at least one of the tissue graft or suture loop to seat the tissue anchor against the surface of the bone.

As in the previous method, inserter rod 120 may also be flexible, to better accommodate patient anatomy and the interaction between the tissue anchor 110 and the inserter rod, although the inserter rod and tissue anchor are already configured in a generally parallel relationship, as in FIG. 3.

In a further embodiment, a method of using tissue anchor 210 includes securing a tissue graft to a suture loop 212; positioning a guide pin 230 within a bone tunnel through a bone such that leading and trailing ends of the guide pin extend past entrance and exit ends of the bone tunnel respectively; removeably affixing an inserter rod 220 to the tissue anchor, the inserter rod may include a longitudinal length and first and second ends, the tissue anchor removeably affixed along the longitudinal length adjacent the first end; removeably affixing the trailing end of guide pin 230 to the first end of the inserter rod; pulling the inserter rod, with tissue anchor affixed, up through the bone tunnel by pulling the leading end of the guide pin; once the tissue anchor exits from the exit end of the bone tunnel to a surface of the bone, removing the guide pin from the inserter rod; removing the inserter rod from the tissue anchor; and pulling on one of the graft or the suture loop to seat the tissue anchor against the surface of the bone.

In one alternate embodiment using tissue anchor 210, the positioning of the guide pin 230 within the bone tunnel may include drilling the guide pin through the bone, passing a reamer (not shown) over the guide pin, whereby reaming over the guide pin forms the bone tunnel, and removing the reamer. Then, the guide pin, still positioned within the formed bone tunnel, may then be secured to the inserter rod and the remainder of the method may be performed.

As discussed above, the inserter rod may include an engagement structure 240, whereby positioning the engagement structure within a channel 215 of the tissue anchor removeably affixes the inserter rod to the tissue anchor. Alternatively, the engagement structure 240 may be positioned within the tissue anchor, and the inserter rod may be passed through the channel 215 and through the engagement structure to removeably affix the tissue anchor 210 to the inserter rod 220.

The method of using tissue anchor 210 may further include an alternative embodiment in regards to the tissue anchor being seated onto the surface of the bone. In this embodiment, with the inserter rod 220 still removeably affixed to the tissue anchor, and upon pulling one of the graft or the suture loop, rotating the tissue anchor relative to the inserter rod such that the tissue anchor rotates to a position that is generally parallel to the bone surface. This rotation may be assisted by an end of the tissue anchor contacting the bone surface while the graft or suture loop is pulled. Additionally, if the second end of the inserter rod is still extending from the entrance end of the bone tunnel, the rod may also be pulled from the second end to assist in seating the tissue anchor. Then, once the tissue anchor is generally seated against the surface of the bone, the inserter rod may be removed. Moreover, as discussed above, the passage of the tissue anchor through the bone tunnel, and subsequent rotation of the tissue anchor at the surface of the bone, may be assisted by a flexible inserter rod 220 such that the tissue anchor and inserter rod will have a smaller profile while within the bone tunnel by the inserter rod bending. Once the tissue anchor exits the bone tunnel, the inserter rod will spring back generally to the original longitudinal shape which may assist in rotating the tissue anchor for seating the anchor on the surface of the bone.

The various embodiments of tissue anchors, inserter rods and related elements may be packaged individually or as a kit or system. For example, tissue anchor 10 and inserter rod 20 may be packaged individually, and assembled by the surgeon, or may be packaged already removeably affixed to one another, such that the surgeon can merely unwrap the kit or system and use it on the patient.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A system for securing soft tissue relative to a bone, comprising:
   a tissue anchor comprising a rectangular body having a top surface, a bottom surface, a channel extending through the body from the top surface to the bottom surface and at an angle other than perpendicular to the top and bottom surfaces, and at least one bore hole extending through the body from the top surface to the bottom surface;
   an inserter rod having a longitudinal length and adapted to be positioned through the channel of the tissue anchor wherein a first portion of the length of the inserter rod extends past the bottom surface, a second portion extends from the bottom surface to the top surface through the channel, and a third portion extends past the top surface; and
   an engagement structure on at least one of the channel or the inserter rod adapted to removeably affix the tissue anchor to the inserter rod.

2. The system of claim 1, wherein the engagement structure comprises a taper along at least the second portion of the longitudinal length of the inserter rod.

3. The system of claim 1, wherein the engagement structure comprises a threaded portion along at least the second portion of the longitudinal length of the inserter rod.

4. The system of claim 3, wherein the engagement structure further comprises a matching threaded portion along at least a portion of an inner surface of the channel.

5. A system for securing soft tissue relative to a bone, comprising:
   a tissue anchor comprising a body having a first longitudinal axis, at least one bore hole and a first engagement structure, the first engagement structure comprising one of a hook or an eyelet; and
   an elongated inserter rod including a second longitudinal axis and a second engagement structure, the second engagement structure comprising the other of the hook or the eyelet to removeably affix the inserter rod to the tissue anchor by positioning the hook within or through the eyelet,
   wherein with the first and second engagement structures affixed to one another, the first and second axes are parallel to one another and spaced apart from one another.

6. The system of claim 5, wherein the engagement structure of the tissue anchor is positioned towards an end portion of the body.

7. The system of claim 5, wherein the engagement structure of the inserter rod is positioned towards an end portion of the inserter rod.

8. A system for securing soft tissue relative to a bone, comprising:
  a tissue anchor comprising a rectangular body having a top surface and a bottom surface extending along a length of the body, the length being greater than a height defined by a distance between the top and the bottom surfaces, at least one bore hole and a channel extending through the body from the top surface to the bottom surface, the channel comprising a first diameter at one end adjacent the top surface, a second diameter at a middle portion, and a third diameter at a second end adjacent the bottom surface, wherein the second diameter is smaller than the first or third diameters;
  an inserter rod having a longitudinal length and adapted to be positioned within the channel of the tissue anchor such that the length of the body is not parallel with the length of the inserter rod; and
  an engagement structure adapted to be positioned within the channel to removeably affix the tissue anchor to the inserter rod.

9. The system of claim 8, wherein the channel passes through the body at a transverse angle to the body.

10. The system of claim 8, wherein the engagement structure is positioned adjacent to the middle portion having the second diameter.

11. The system of claim 8, wherein the engagement structure comprises a substantially cylindrical shape having a throughbore and adapted to rotate while positioned within the channel.

12. The system of claim 11, wherein the inserter rod is adapted to pass through the throughbore of the engagement structure such that the inserter rod extends from both ends of the channel.

13. The system of claim 12, wherein the inserter rod further comprises a threaded portion along at least a portion of the longitudinal length, and the engagement structure further comprises a matching threaded portion positioned along at least a portion of the throughbore to releaseably affix the engagement structure to the inserter rod.

14. The system of claim 13, the system further comprising a guide pin which is removeably affixed to the inserter rod.

15. The system of claim 13, wherein the tissue anchor and inserter rod can rotate relative to one another until the ends of the inserter rod contact an inner surface of the channel defined by the first and third diameters.

16. The system of claim 8, wherein the inserter rod and engagement structure are fixedly secured to one another.

17. The system of claim 16, wherein the engagement structure is adapted to be removeably affixed within the channel of the tissue anchor by a press-fit.

* * * * *